United States Patent
Koo et al.

(10) Patent No.: US 6,779,410 B2
(45) Date of Patent: Aug. 24, 2004

(54) SAMPLE HOLDER AND AUXILIARY APPARATUS

(75) Inventors: Bon-Se Koo, Kyungki-do (KR); Ho-Hyung Jung, Kyungki-do (KR); Dae-Jung Kim, Kyungki-do (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 10/176,426

(22) Filed: Jun. 19, 2002

(65) Prior Publication Data

US 2002/0194938 A1 Dec. 26, 2002

(30) Foreign Application Priority Data

Jun. 20, 2001 (KR) ........................................ 2001-35111

(51) Int. Cl.[7] ................................................ G01N 1/00
(52) U.S. Cl. ...................................................... 73/863
(58) Field of Search ............................ 73/863, 864.41, 73/864.42, 864.44, 864.45, 864.63, 864.65, 864.67, 864.91; 250/288, 358.1, 359.1, 360.1, 311

(56) References Cited

U.S. PATENT DOCUMENTS 2,298,627 A * 10/1942 Proudman et al. ....... 73/864.63
4,634,866 A * 1/1987 Conway ...................... 250/288
4,790,197 A * 12/1988 Kimonides ............... 73/864.65
5,341,693 A * 8/1994 Banu ....................... 73/864.67

FOREIGN PATENT DOCUMENTS

JP 404074946 * 3/1992 ................... 73/863

* cited by examiner

Primary Examiner—Robert Raevis
(74) Attorney, Agent, or Firm—Marger Johnson & McCollo, P.C.

(57) ABSTRACT

A sample holder and auxiliary apparatus are provided to position and hold a sample in the sample holder. A method of positioning and holding a sample in the sample holder is also provided. The sample holder preferably includes a holder body having a sample holding portion arranged therein. An opening in the sample holding portion is configured to receive a sample therein. An elastic member is configured to supply a holding force to hold the sample in the opening. The auxiliary apparatus preferably includes one or more holder supports configured to support a sample holder. The auxiliary apparatus is configured to receive the sample holder and force a sample holding member of the sample holder into a rearward position to permit the sample holder to receive a sample into an opening thereof.

24 Claims, 9 Drawing Sheets

SAMPLE HOLDER AND AUXILIARY APPARATUS

This invention claims priority from Korean Patent Application No. 2001-35111, filed Jun. 20, 2001, the contents of which are incorporated herein by reference in their entirety.

BACKGROUND OF THE INVENTION

1. Field of the Invention

The present invention relates to a vertical scanning electronic microscope (SEM) used to conduct a surface analysis of a sample. More particularly, this invention relates to a sample holder used in the vertical SEM. The present invention further relates to an auxiliary apparatus for holding a sample in the sample holder and to a method of loading a sample in the sample holder using the same.

2. Description of the Related Art

To manufacture a semiconductor integrated circuit, a semiconductor layer pattern multi-layer, an insulating layer pattern, and a conductive layer pattern are formed on a wafer where the integrated circuit will be implemented. A scanning electronic microscope (SEM) is generally used to inspect and analyze the patterns formed during each process. To analyze a wafer, the wafer is first cut to a proper size to produce a sample. The surface and cut section of the wafer are then analyzed in the SEM. A sample holder is used to mount the sample in a predetermined position in the SEM.

Figure 1:
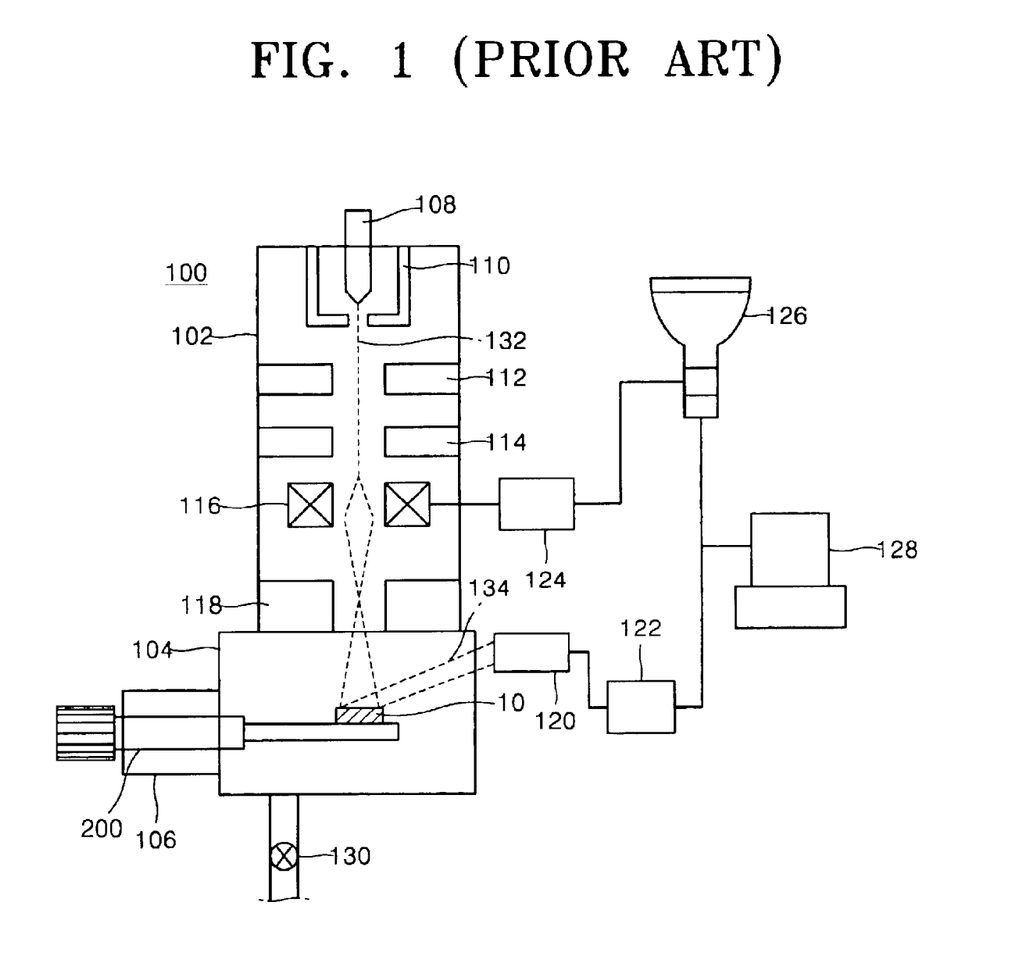
FIG. 1 is a schematic block diagram illustrating a conventional vertical scanning electron microscope (SEM)

FIG. 1 is a schematic diagram illustrating the configuration of a conventional vertical scanning electronic microscope (SEM) 100. An SEM 100 uses various electronic lenses to focus an electron beam light source onto the sample. Using the focused electron beam, the SEM 100 scans a desired portion of a sample and detects various signals, such as secondary electrons, back scattering electrons, or X-rays, that are emitted from the sample. The SEM 100 then image-processes the signals to generate a magnified image of the desired area.

Referring to FIG. 1, the SEM 100 includes a sample chamber 104, which receives a sample 10 held in a sample holder 200. An electron gun 108 generates an electron beam 132, which is directed through a column portion 102 into the sample chamber 104. An electron beam guide 110, formed in the column portion 102, guides the electron beam 132 in the desired direction. Anodes 112, focusing lenses 114, deflection coils 116, and objective lenses 118 are sequentially formed below the electron beam guide 110. An end of the electron gun 108 includes a filament tip for generating the electron beam 132.

A shutter (not shown) is positioned in a lower end of the objective lens 118 to control the supply of the electron beam 132. The electron beam 132 generated in the electron gun 108 is accelerated and focused. The depth of focus is adjusted using an objective iris (not shown) in the objective lens 118. The electron beam 132 scans the sample 10 mounted on a sample holder 200. Secondary electrons 134 generated by the sample 10 are detected by a detector 120.

The detected electronic signals are amplified using an amplifier 122 and displayed as an image on a display screen. The signals are transferred, for instance, to a cathode-ray tube 126 and scanned onto an inner fluorescent screen thereof. A surface image of the sample 10 is thereby displayed. A deflection angle is controlled by a deflection coil (not shown) in the cathode-ray tube 126.

In the SEM 100, a scanning plane of the sample 10 is decomposed into delicate pixels, and electronic signals corresponding to the pixels are transmitted clockwise to generate a screen image. The electronic signals that are passed through the amplifier 122 are transmitted into a scanning circuit 124. A deflection angle of the electron beam 132 is controlled in the deflection coil 116 of the column portion 102. In addition, the electron signals that are passed through the amplifier 122 are transmitted into an image transmission portion 128 to display the image.

A turbo pump 130 is installed in a lower end of the sample chamber 104 to maintain the sample chamber 104 in a vacuum state. A preliminary chamber 106 is installed on the side of the sample chamber 104 to maintain the vacuum state when the sample holder 200 is loaded or unloaded into the sample chamber 104.

Figure 2:
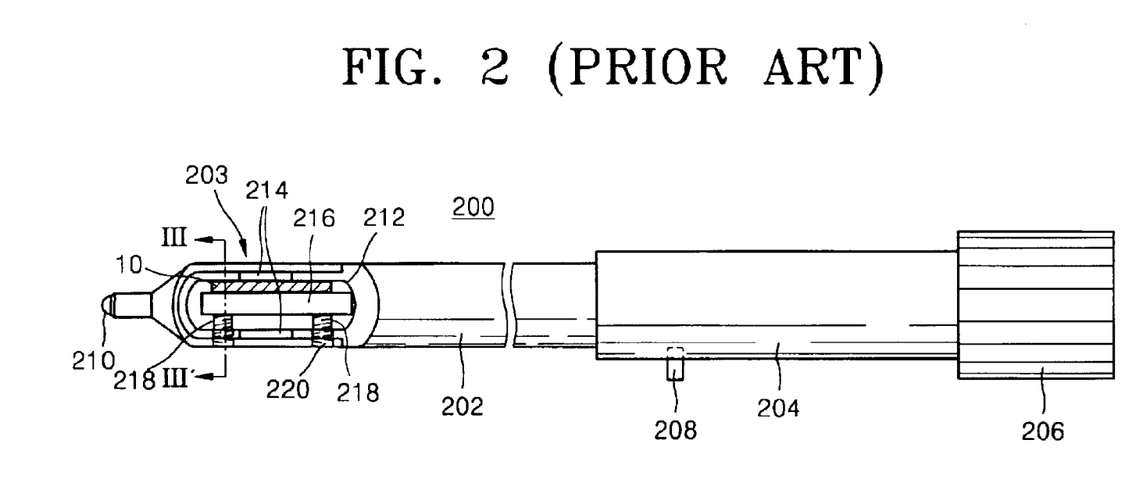
FIG. 2 is a schematic plan view of a conventional sample holder.
Figure 3:
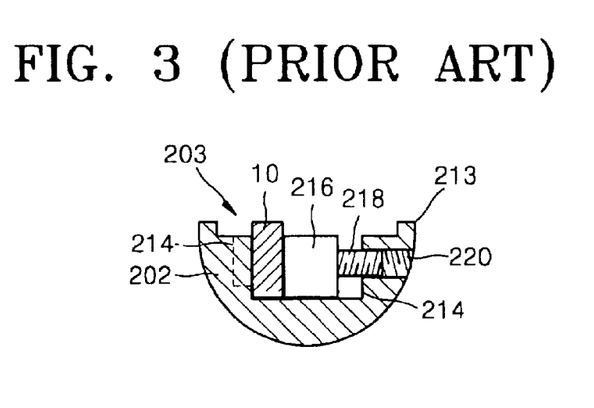
FIG. 3 is a cross-sectional view of the conventional sample holder of FIG. 2, taken along line III-III'.

FIG. 2 is a schematic plan view of a conventional sample holder 200 (e.g., model S-5000 manufactured in Japan by Hitachi). FIG. 3 is a cross-sectional view of the sample holder 200 taken along line III-III' of FIG. 2. Referring to FIGS. 2 and 3, the body of the sample holder 200 has a generally circular, rod-like shape. A sample holding portion 203, formed in a forward portion of the sample holder 200, is configured to receive and hold a sample 10.

A sapphire tip 210 is formed at the forward end of the sample holder 200. A handle 206 is formed at a rearward end of the sample holder 200. The body of the sample holder 200 has a first body portion 202, which includes a sample holding portion, and a second body portion 204. The second body portion 204 is larger in diameter than the first body portion 202. The first and the second body portions 202, 204 can be attached to and separated from each other.

The sample holding portion 203 is typically formed by horizontally removing an upper portion of the first body portion 202. A ridge 213, having a predetermined height, may be formed around the edge of the sample holding portion 203. A sample insertion groove 212 is formed to a predetermined depth in the sample holding portion 203 to receive and hold the sample. Sample insertion auxiliary grooves 214 are provided on both sides of the sample insertion groove 212. The auxiliary grooves 214 facilitate the insertion and removal of a sample 10 using forceps. Screw holes 220 are formed through a sidewall of the sample insertion groove 212.

In the conventional sample holder 200, the sample 10 is inserted along one side of the sample insertion groove 212. An aluminum spacer 216 is also inserted into the sample insertion groove 212, and contacts a side of the sample 10. Two copper set screws 218 are inserted through the holes 220 into contact with a sidewall of the spacer 226. The screws 218 are advanced through the holes 220 to force the spacer 216 into close contact with the sample 10, thereby holding the sample 10 in place.

To use the conventional sample holder 200, a wafer is first cut at a desired location to produce a sample having a size of around 5–10 mm×4–6 mm. The sample 10 is positioned vertically in the center of the sample insertion groove 212 using forceps. The spacer 216 is then inserted into the insertion groove 212 along a side of the sample 10, in the same manner. The screws 218 are then advanced through the screw holes 220 to force the spacer 216 into close contact with the sample 10. The sample 10 is thereby held in place between a sidewall of the sample insertion groove 212 and the spacer 216. A driver (e.g., a flathead screwdriver) is used to drive the screws 218 into the holes 220.

Unfortunately however, because the conventional sample holder 200 uses the screws 218 to hold the sample 10 in place, several problems occur. Among other things, a tightening force applied to the screw 218 by the screwdriver is transferred to the sample 10 through the spacer 216. The tightening force can cause the sample 10 to be broken. Broken sample particles can cause leaks in the various O-rings in the sample chamber 104 (see FIG. 1). Because the sample chamber 104 is maintained in a high vacuum state, breaches in the O-ring seals permit external air to flow into the sample chamber 104 and reduce the vacuum state of the sample chamber 104. The performance of the turbo pump 130 is also lowered as a result of breeches in the O-ring seals.

In addition, external gas molecules that flow into the sample chamber 104 move into the column portion 102 and are adsorbed to the filament tip of the electron gun 108. The filament tip must then be heated and flashed to remove the adsorbed gas molecules. Flashing current directed into the tip causes the tip to wear out, and thereby reduces the life of the tip. Reduction of the life of the tip shortens a period between tip replacement and thus causes a decrease in the running time of production facilities.

In addition, to position the sample 10 in the conventional sample holder 200, a worker must use both hands to operate the driver and hold the forceps. The conventional process of securing a sample 10 in the sample holder 200 includes approximately ten steps and requires a skilled worker. Furthermore, since a force for tightening the screw 218 is not constant, the force is frequently either too large or too small. Damage to the sample 10 may occur when the strength of the tightening force is too large. Separation of the sample 10 from the sample holder 200 may occur when the force is too small.

In addition, the screws 218 are repeatedly driven in and out of the screw holes 220, causing the screws 218 and the walls of the screw holes 220 to become worn out over time. The deterioration of the screws 218 means that they must periodically be replaced. Production costs increase as the cost of components increases. Also, the deterioration of the screws 218 and screw holes 220 results in the generation of particles that can interfere with the testing process. The deterioration also reduces a tightening force of the screws 218. As the tightening force is reduced, the sample 10 may become separated from the sample holder 200.

SUMMARY OF THE INVENTION

To solve the above problems, one object of the present invention is to provide a sample holder that prevents a sample from being broken. This can be accomplished, for instance, by using an elastic member having a predetermined elasticity to provide the holding force, rather than a screw.

Another object of the present invention is to provide a sample holder in which the process of inserting and removing a sample is simplified, such that the number of steps of the process can be reduced.

Yet another object of the present invention is to provide an auxiliary apparatus for holding a sample holder in a way that allows a sample to be easily inserted into and removed from the sample holder.

Still another object of the present invention is to provide an improved method of holding a sample in a sample holder.

According to one embodiment of the invention, a sample holder includes a body, a first opening, and a holding mechanism. The holder body preferably has a circular, rod-like shape. A sample holding portion is preferably formed in a forward end of the holder body.

The first opening preferably includes a longitudinal groove formed in an upper side of the sample holding portion. A sample is inserted into and held in the first opening. The holding mechanism preferably includes a sample holding member arranged to contact a side of the sample mounted in the first opening. An elastic member is preferably used to force the holding member into contact with the sample and hold the sample in the first opening.

The elastic member can, for example, be either a compression member or a tension member. If a compression member is used, an elastic member insertion groove is preferably formed in the holder body to communicate with a second opening, in which the sample holding member is disposed. One end of the elastic compression member is inserted into the elastic member insertion groove while the other end of the compression member contacts the sample holding member. The elastic member biases the sample holding member in a forward position.

The sample holding member preferably has a main body and a projection (or lip). The main body is arranged to contact a longitudinal end of the sample and the projection is arranged to contact a lateral side of the sample. A first protrusion can be formed on the upper surface of the main body.

An auxiliary apparatus can also be provided to assist with positioning a sample in a sample holder. The auxiliary apparatus preferably includes a base and one or more supports. The supports are arranged on the base to support a sample holder. Stops can be arranged to facilitate proper and secure positioning of the sample holder in the auxiliary apparatus.

One stop, for instance, can be arranged to stop forward movement of the sample holding member. Another stop can be used to stop further forward movement of the sample holder. And another stop can be used to prevent backwards movement of the sample holder while a sample is being inserted into the holder.

A method of holding a sample in a sample holder can comprise mounting the sample holder on supports of an auxiliary apparatus. The sample holder is moved forward with respect to the auxiliary apparatus. As the sample holder moves forward, a protrusion on a sample holding member catches on a stop, holding the sample holding member back as the rest of the sample holder moves forward. A catch, located on the sample holder, catches on another stop (or latch) to prevent backward movement of the sample holder.

While the sample holding member is held rearward, the sample is mounted in a first opening. Once the sample is positioned in the first opening, the latch is released to permit removal of the sample holder from the auxiliary apparatus. The sample, mounted in the first opening, is held in place by an elastic force applied by an elastic member.

According to the preferred embodiments of the present invention, a sample can be held in a sample holder by a constant elastic force. Separation of the sample from the sample holder can be effectively prevented while providing improvements over the prior art. In particular, the use of the elastic force avoids the use of the non-constant tightening force applied by screws. The breaking of samples can thereby be prevented.

BRIEF DESCRIPTION OF THE DRAWINGS

The foregoing and additional objects and advantages of the present invention will become more readily apparent through the following detailed description of preferred embodiments, made with reference to the attached drawings, in which:

FIGS. 9 through 11 illustrate a process of inserting a sample into the sample holder of FIG. 4 using the auxiliary apparatus of FIG. 7, wherein:

FIGS. 12 through 15 are schematic plan views illustrating a method of inserting and holding a sample in the sample holder of FIG. 4 using the auxiliary apparatus of FIG. 7, wherein:

DETAILED DESCRIPTION OF PREFERRED EMBODIMENTS

The principles of the present invention will be described more fully hereinafter with reference to preferred embodiments thereof. It should be noted, however, that the following embodiments may be modified in various forms, and that the scope of the present invention is not limited to these specific embodiments. The embodiments of the present invention are provided by way of example, and not by way of limitation.

Figure 4:
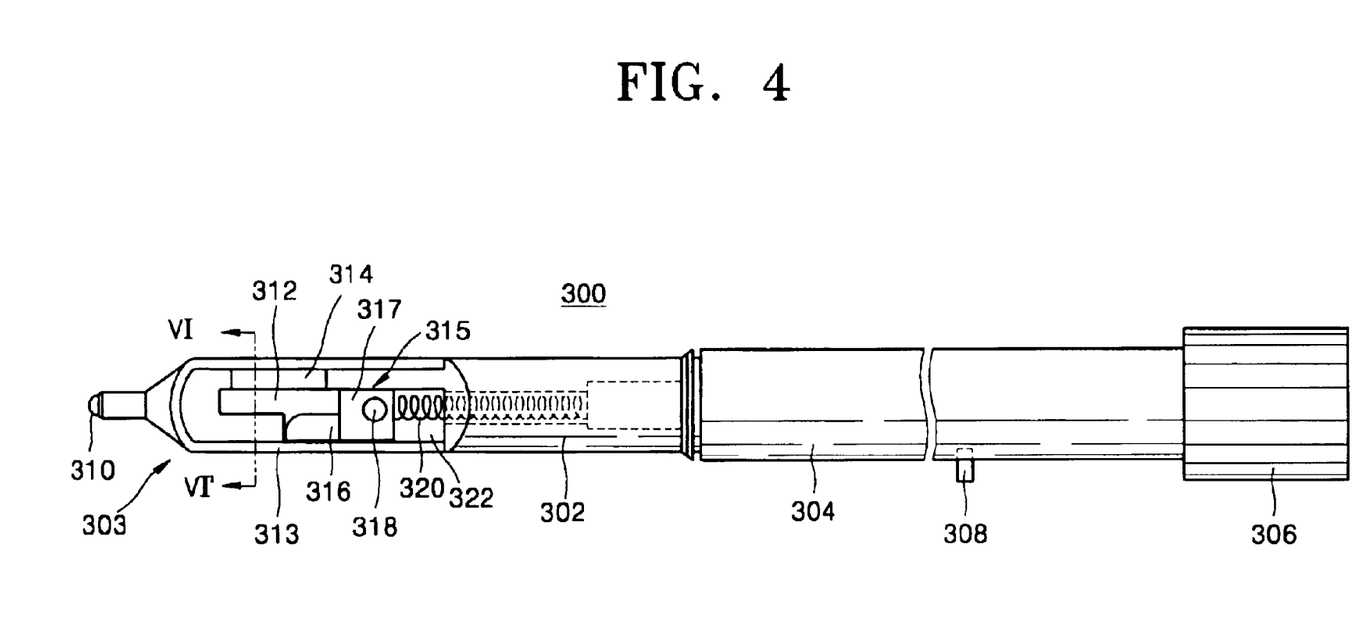
FIG. 4 is a schematic plan view of a sample holder according to one embodiment of the present invention.
Figure 5:
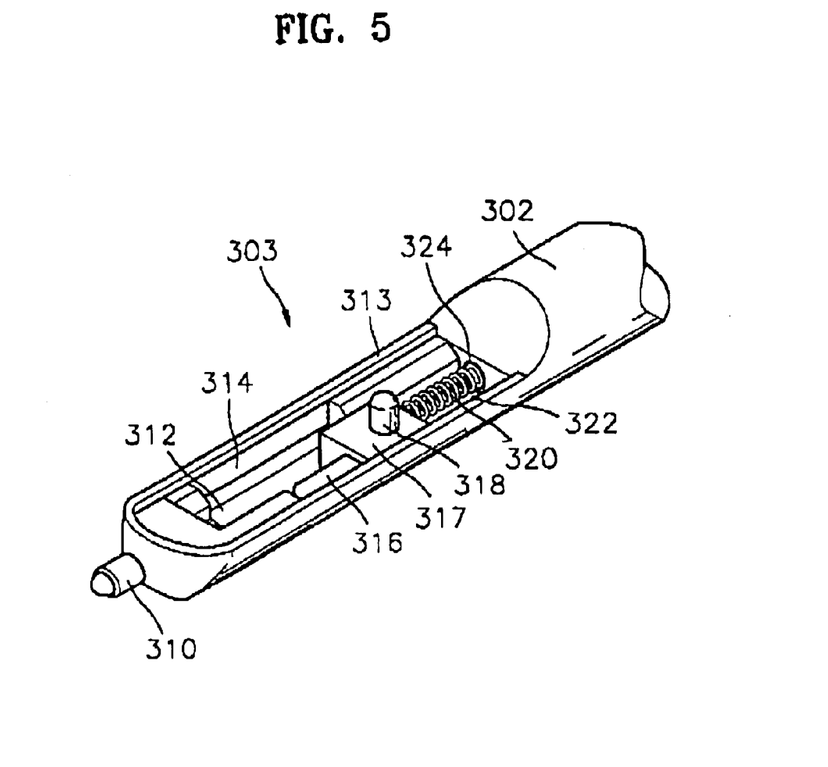
FIG. 5 is an enlarged perspective view of a sample holding portion of the sample holder shown in FIG. 4.
Figure 6:
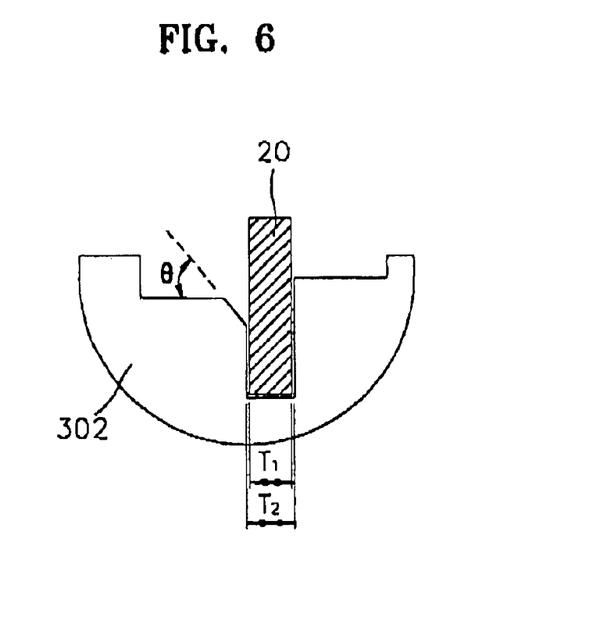
FIG. 6 is a cross-sectional view of the sample holder of FIG. 4, taken along line VI-VI'.

One embodiment of the invention will now be described with reference to FIGS. 4 through 6. FIG. 4 is a schematic side view of a sample holder 300 constructed according to a first embodiment of the present invention. FIG. 5 is an enlarged perspective view of a sample holding portion 303 of the sample holder 300 of FIG. 4. FIG. 6 is a cross-sectional view of the sample holder 300 of FIG. 4, taken along line VI-VI', and illustrates the positioning of a sample 20 in a first opening 312.

As shown in FIGS. 4 through 6, the body of the sample holder 300 has a generally circular, rod-like shape. A body of the sample holder 300 includes a first body member 302 and a second body member 304. The first body member 302 and the second body member 304 can be coupled together or separated from each other. In the preferred embodiment, the second body member 304 is slightly larger in diameter than the first body member 302, but other configurations are also contemplated. A handle 306 is formed in the second body member 304 at the rear of the sample holder 300. A sapphire tip 310 is formed at the forward end of the first body member 302. A protrusion (or catch) 308 is formed in the middle of the second body member 304. The catch 308 is arranged to contact a sensing member of a preliminary chamber 106 to determine when the sample holder 300 is properly mounted in a sample chamber 104 (see FIG. 1).

A sample holding portion 303 is formed in a forward portion of the first body member 302 of the sample holder 300. An upper portion of the forward part of the first body member 302 is removed to form the sample holding portion 303. A ridge 313, having a predetermined height, is preferably arranged around the edge of the sample holding portion 303. A first opening 312 includes a groove having a predetermined depth and a length extending parallel to the length of the sample holder 300. The first opening 312 receives and holds the sample. In this embodiment, the width "T" of the first opening 312 is preferably about 0.9 mm and the thickness "T1" of the sample is preferably about 0.8 mm. The width and depth of the first opening 312 may be selected and formed in any desired configuration, however, depending on the size of a desired sample. The length of the first opening 312 is adjusted to match the size of the sample by forward or backward movement of a sample holding member 315 of a holding mechanism.

A second opening 322 is formed in the sample holding portion 303 in communication with the first opening 312. The second opening 322 also includes a groove that extends parallel to the length of the sample holder 300. The sample holding member 315 is located in the second opening 322. The sample holding member 315 preferably includes a lower lip 316 and a main body 317 that are arranged having a stair-step shape (in plan view). The holding mechanism also includes an elastic member 320 (e.g., a compression spring), which applies an elastic force to the main body 317 to hold the sample 20 in place in the first opening 312.

More particularly, the sample holding member 315 includes a lower lip 316 that is thinner than the main body 317 of the sample holding member 315. The lower lip 316 of the sample holding member 315 is also preferably shorter than the main body 317 of the sample holding member 315 such that scanning of electron beam is not disturbed when tilting the sample holder 300 to analyze a sample 20 in a scanning electron microscope (SEM). The sample holding member 315 holds a sample 20 mounted in the first opening 312 by applying force in the direction of the length of the sample holder 300 through the main body 317. In addition, the lower lip 316 is preferably configured to provide force on the sample 20 in the direction of the width of the sample holder 300 to help hold the sample 20 more firmly in place, but the lower lip 316 is not essential.

A protrusion 318 extends to a predetermined height from an upper side of the main body 317 of the sample holding member 315. An elastic member insertion groove 324 is formed in the first body member 302 to receive and hold the elastic member 320. When the elastic member 320 is a compression spring, it may be inserted into the elastic member insertion groove 324 from the front, or may be inserted into a rearward end of the elastic member insertion groove 324 after removing the second holder member 304 from the first holder member 302.

Although the elastic member 320 is preferably a compression spring, a tension spring could also be used with an attachment point arranged in a predetermined position at the forward end of the first body member 302. In this alternate embodiment, a tension-resistant force from the spring is applied to the sample holding member 315 to hold the sample 20 in place.

A third opening 314 is also preferably arranged next to the first opening 312. The third opening can again be a groove arranged in the direction of the length of the sample holder 300. The third opening 314 is preferably formed near a side of sample holder 300 adjacent to the first opening 312. The depth of the third opening 314 is preferably less than that of the first opening 312, and is designed such that the sample 20 can be easily inserted into or removed from the first opening 312 using forceps. A corner formed by the interface between the first and third openings 312, 314 is preferably beveled at an angle "θ" sufficient to permit a wafer to be easily inserted into the first spaced part. Alternatively, the corner may be rounded.

Figure 7:
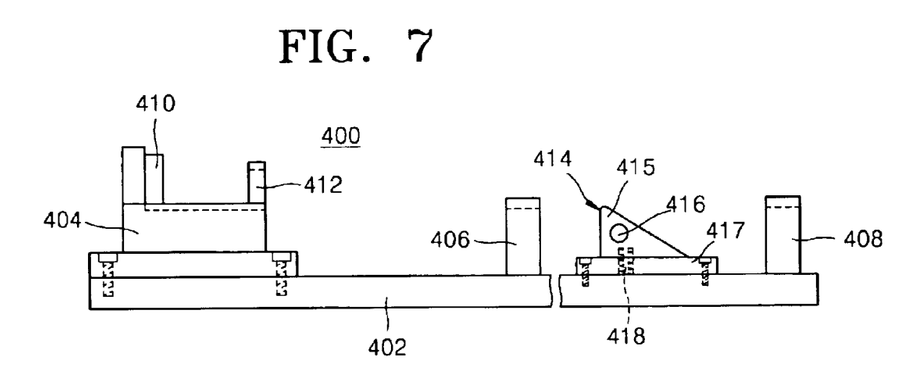
FIG. 7 is a schematic side view of an auxiliary apparatus for holding a sample in a sample holder according to another aspect of the present invention.
Figure 8:
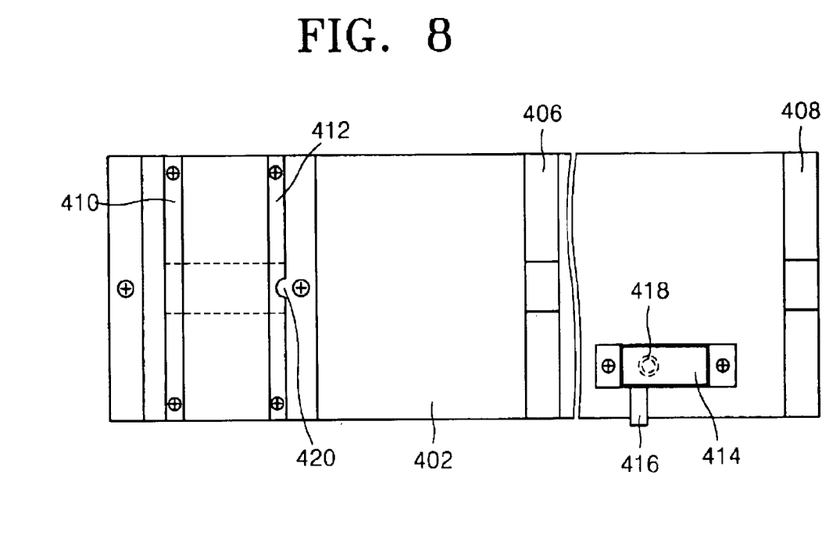
FIG. 8 is a schematic plan view of the auxiliary apparatus shown in FIG. 7.

FIG. 7 is a schematic side view of an auxiliary apparatus 400 configured to facilitate insertion of a sample into the sample holder 300, shown in FIG. 4, according to another aspect of the present invention. FIG. 8 is a schematic plan view of the auxiliary apparatus 400 of FIG. 7. Referring to FIGS. 7 and 8, a first holder support 404, a second holder support 408, and a third holder support 406, each having a predetermined height, are arranged on a plastic base 402. The holder supports 404, 408, 406 are each separated from an adjacent support by a predetermined distance. Semicircular grooves are provided in the center of the upper surfaces of the holder supports 404, 408, 406 to stably support the sample holder 300.

The forward end of the upper surface of the first holder support 404 includes a wall that prevents the sapphire tip 310 of the sample holder 300 from moving forward past a predetermined point. A first stop 412 is arranged at a predetermined distance along the upper surface of the first holder support 404. A semicircular groove 420 is formed in the first stop 412 to receive the protrusion 318 formed on the upper surface of the sample holding member 315 as the sample holder 300 is moved forward in the auxiliary holder 400.

In addition, an auxiliary stop 410 may be arranged adjacent the wall of the first support 404, to contact the sapphire tip of the sample holder 300 and arrange the protrusion 318 in the proper position with respect to the first stop 412. The second holder support 408 and the third holder support 406 have much the same shape as each other and are each secured to the base 402 by a respective bolt. The third holder support 406, positioned near the center of the auxiliary apparatus, is optional and need not be included.

A latch 414 includes a latch base 417 and a latching member 415. The latch base 417 is bolted onto the base 402 of the auxiliary apparatus 400 between the second holder support 408 and the third holder support 406. The latching member 415 preferably includes a triangular-shaped body having an upwardly slanting edge and a vertical edge that drops downward from a forward end of the slanted edge. The latch 414 is preferably capable of upward and downward movement relative to the base 402. An elastic member 418, such as a compression spring, can be arranged in the latch base 417 to bias the latching member 415 in an upward position.

As the sample holder 300 is inserted into the auxiliary holder 400, the catch 308, formed on a lower external surface of the sample holder 300, depresses the latching member 415 of the latch 414. After the catch 308 passes the latch 414, the latching member 415 is released and springs back into its original, upward position. The latch 414 thereby operates to prevent backward movement of the holder 300. A handle 416 can be formed on a side of the latch 414 to permit a user to manually initiate downward movement of the latching member 415 to release the catch 308 and permit removal of the holder 300.

Figure 9:
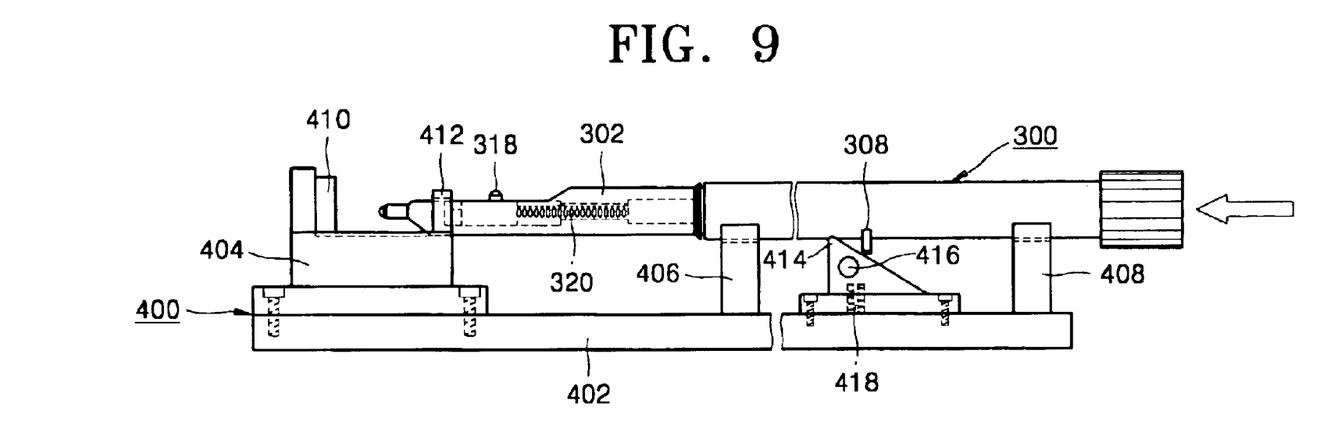
FIG. 9 is a schematic side view illustrating the sample holder of FIG. 4 placed on the auxiliary apparatus of FIG. 7.
Figure 10:
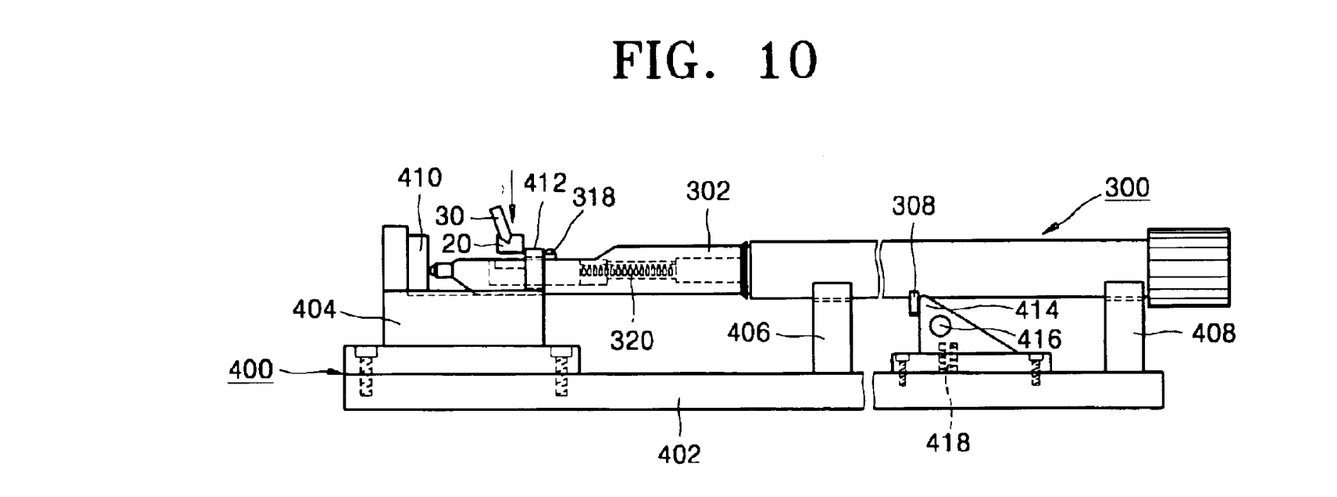
FIG. 10 is a schematic side view showing the sample holder of FIG. 4 being positioned on the auxiliary apparatus of FIG. 7 in a manner that permits the insertion of a sample in the sample holder.
Figure 11:
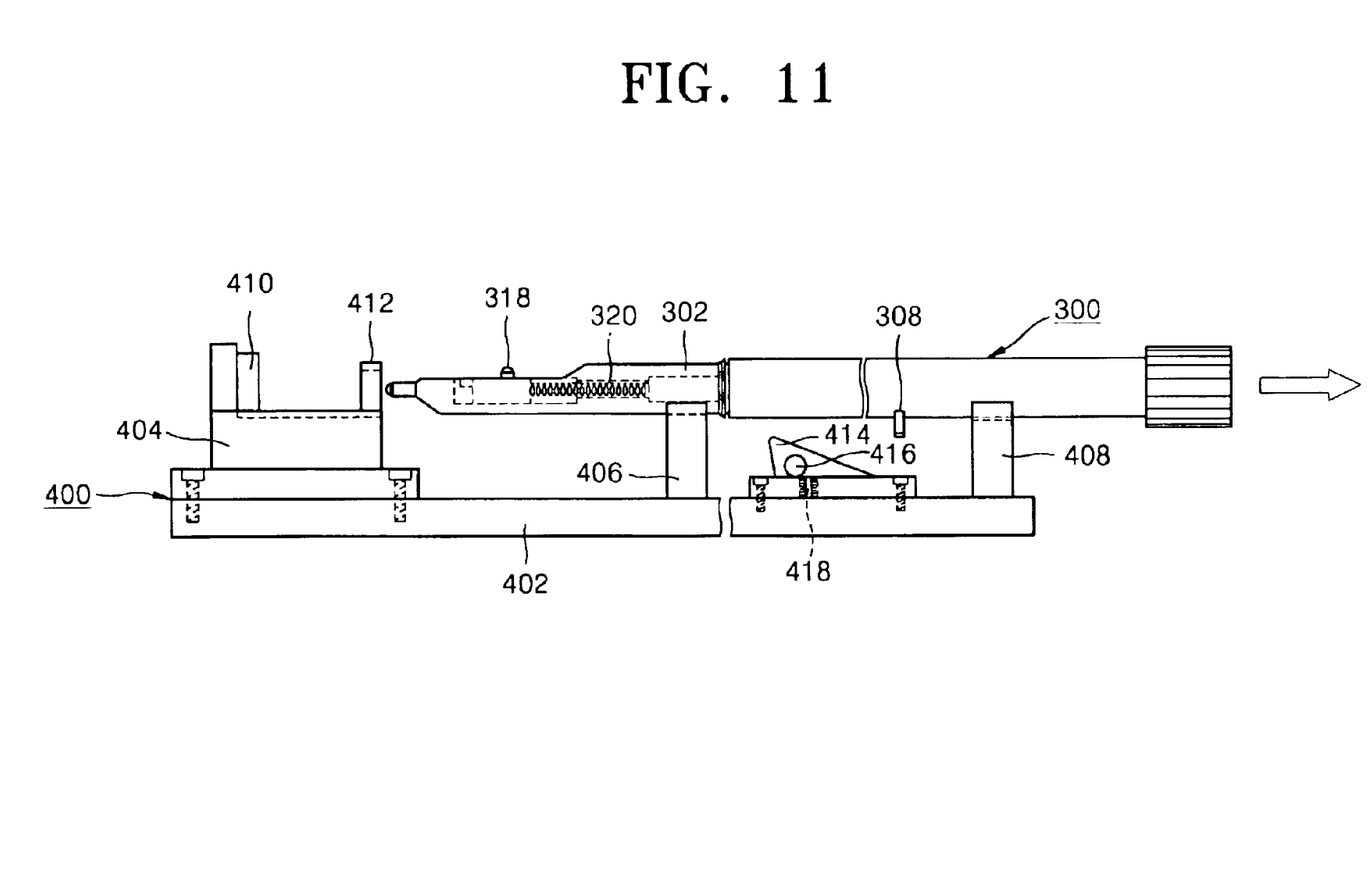
FIG. 11 is a schematic side view showing the sample holder of FIG. 4 being removed from the auxiliary apparatus of FIG. 7, after having a sample placed therein.

A method of mounting the sample holder 300 in the auxiliary apparatus 400 will now be described in greater detail with reference to FIGS. 9 through 11. FIG. 9 illustrates the sample holder 300 being positioned on the auxiliary apparatus 400. FIG. 10 illustrates the sample holder 300 located in a forward position on the auxiliary apparatus 400 to receive a sample into the sample holder 300. FIG. 11 illustrates the sample holder 300 being withdrawn from the auxiliary apparatus 400.

Referring to FIG. 9, the sample holder 300 is mounted along the semicircular grooves formed on the upper surfaces of the first, second, and third holder supports 404, 408, 406. A forward end of the sample holding portion is inserted into a hole formed in the first stop 412.

Referring to FIG. 10, the sample holder 300 is moved forward in the auxiliary apparatus 400 until the tip contacts the auxiliary stop 410. As a worker grips the handle 306 and moves the sample holder 300 forward in the auxiliary apparatus 400, the catch 308 on the second body member 304 moves along the upwardly slanted edge of the latching member 415 of the latch 414. The latching member 415 is thereby forced downward by the catch 308. As the catch 308 passes the forward end of the slanted edge, the force of the catch 308 on the latching member 415 is released, and the elastic member 418 forces the latching member 415 upward into its original position. The catch 308 is thereby caught on the latch 414 to prevent the sample holder 300 from being prematurely removed.

Furthermore, as the holder 300 is moved forward into the apparatus 400, the first protrusion 318, formed on the upper surface of the first body member 302, catches within the groove 420 of the first stop 412. Accordingly, as the sample holder 300 moves forward, the sample holding member 315 is held back, compressing the elastic member 320 in the first body member 302. When the holder 300 is moved forward and the sample holding member 315 is held back, the first opening 312 is lengthened to receive the sample 20. The worker then uses forceps 30 to insert the sample 20 into the first opening 312.

Referring to FIG. 11, to release the holder 300 from the auxiliary apparatus 400, the worker depresses the latch handle 416. The catch 308 is thereby released from the latch 414, permitting backward movement of the sample holder 300. As the holder 300 is withdrawn from the apparatus 400, the first protrusion 318 is removed from the first stop 412 and the elastic member 320 forces the sample holding member 315 towards its original position, thereby clamping and holding the sample in the first opening 312. After the sample 20 is loaded and held in the sample holder 300, the sample holder 300 can be positioned in the sample chamber 104 (see FIG. 1) and a sample analysis can be performed.

Figure 12:
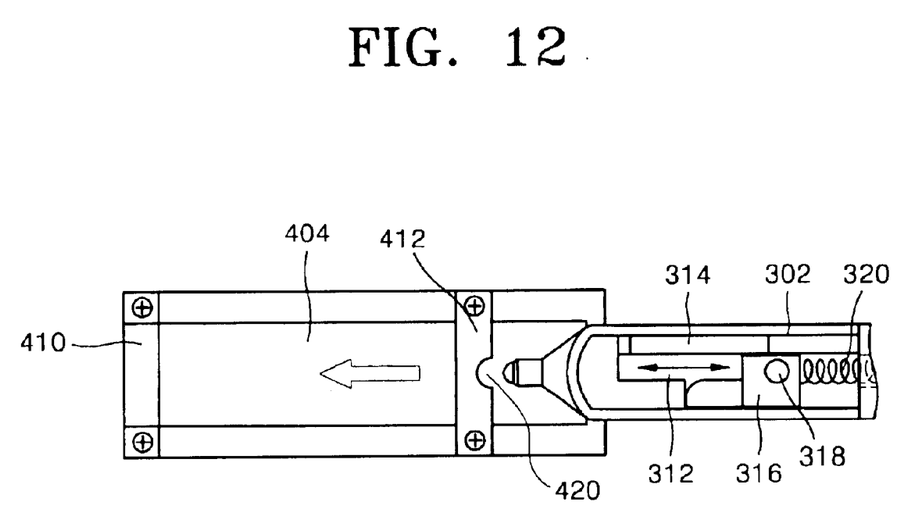
FIG. 12 is a schematic plan view illustrating the sample holder of FIG. 4 being moved into a sample loading position in the auxiliary apparatus of FIG. 7.

FIGS. 12 through 15 are schematic plan views of the sample holder 300 and auxiliary apparatus 400. These figures further illustrate the method of positioning the sample 20 in the sample holder 300 using the auxiliary apparatus 400. Referring to FIG. 12, the force of the elastic member 320 biases the sample holding member 315 towards the forward end of the sample holder 300. When the sample holding member 315 is in this position, a length of the first opening 312 is minimized.

Figure 13:
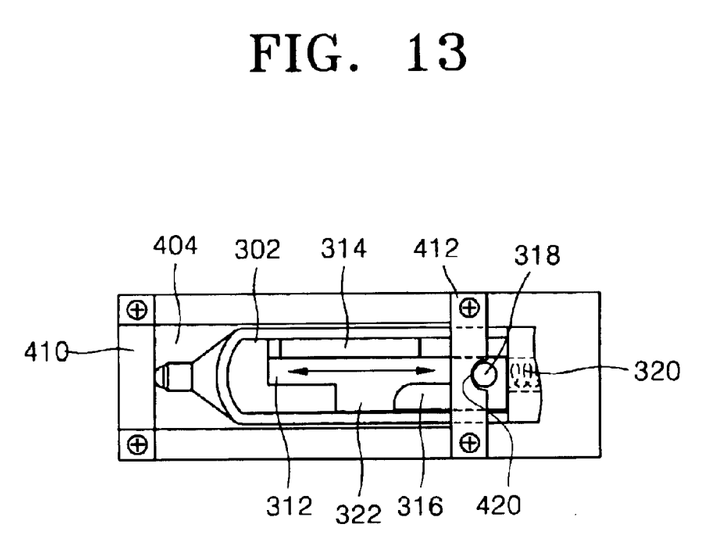
FIG. 13 is a schematic plan view showing the sample holder of FIG. 4 positioned in the auxiliary apparatus of FIG. 7 in a manner that facilitates the insertion of the sample.
Figure 14:
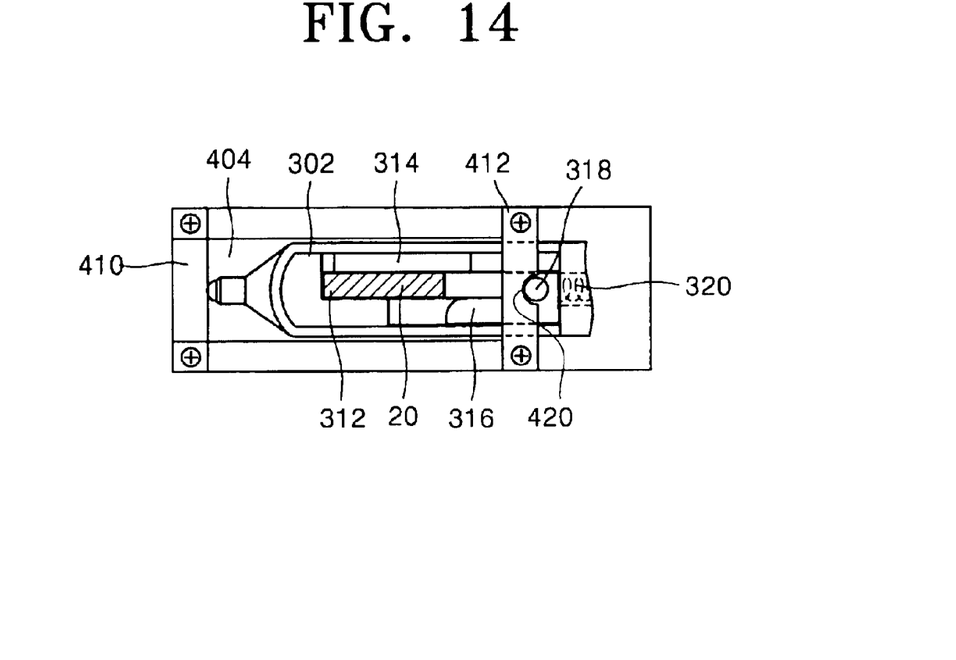
FIG. 14 is a schematic plan view showing a sample placed in the sample holder positioned in the auxiliary apparatus as shown in FIG. 13.

Referring to FIG. 13, as the sample holder 300 is positioned at the forward end of the auxiliary apparatus 400, the first protrusion 318 is caught in the recess 420 of the first stop 412, forcing the sample holding member 315 rearwards in the sample holder 300. The first opening 312 is thereby enlarged to receive the sample 20, and the worker then inserts the sample 20 into the first opening 312, as shown in FIG. 14.

Figure 15:
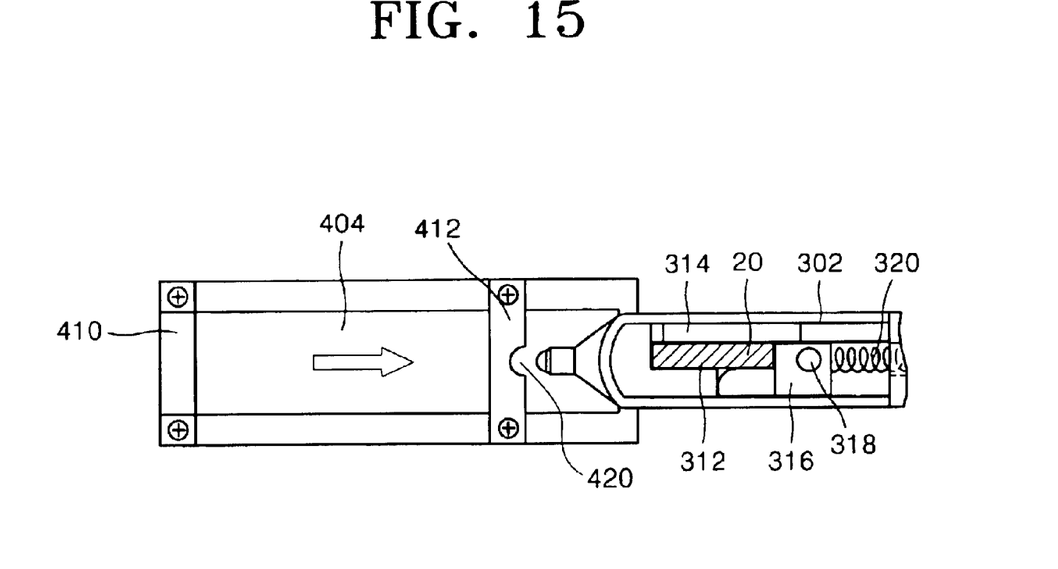
FIG. 15 is a schematic plan view illustrating the sample holder of FIG. 4 being removed from the auxiliary apparatus of FIG. 7, after receiving a sample therein.

Referring to FIG. 15, when the sample holder 300 is subsequently removed from the auxiliary apparatus 400, the compression-resistant elastic force of the elastic member 320 causes the sample holding member 315 to return towards its original position, clamping the sample 20 in place within the first opening 312. The sample 20 is thereby securely retained in the first opening 312.

Various preferred embodiments of the present invention have been described above in detail. It should be noted, however, that the present invention is not limited to these specific embodiments. Various changes to the form and details thereof may therefore be made thereto without departing from the spirit and scope of the invention.

Among other variations, the elastic member 320 may be a tension spring rather than a compression spring. In this alternate embodiment, one end of the tension spring could be attached to a predetermined point near the forward end of the holder 300 with the other end attached to the sample holding member 315. A tension-resistant force of the elastic member 320 biases the sample holding member 315 in a forward position.

In another alternate embodiment, the latch 414 need not include an elastic member 418, but can instead have the latching member 415 permanently disposed in an upward position. In this embodiment, the sample holder 300 may be rotated either clockwise or counterclockwise so that the catch 308 can be moved forward past the latch 414. Once the second protrusion 308 has been moved past the latch 414, the sample holder 300 may then be rotated back to its original position such that the second protrusion 308 catches on the vertical edge of the latching member 415 to prevent backwards movement of the sample holder 300.

According to the preferred embodiment, an elastic member is used to hold the sample in place, thereby providing a more reliable holding force. In addition, the force of the elastic member is automatically controlled according to the size of the sample, preventing the sample from being broken. By preventing broken sample particles from being introduced into the sample chamber, leaks from O-rings in the sample chamber of the SEM can be prevented. The sample chamber can thereby be used for a longer time without degradation in the vacuum characteristics of the chamber. External gas molecules are also prevented from entering the sample chamber, increasing the lifetime of the filament tip of the electron gun.

In addition, using an auxiliary apparatus as described above, the number of steps required to position a sample in a sample holder can be dramatically reduced. The sample can therefore be more easily replaced, and the possibility of human error is also remarkably reduced. In addition, by avoiding the use of consumable parts such as screws, the cost of parts can also be reduced.

While the principles of this invention have been shown and described with reference to preferred embodiments thereof, it will be understood by those skilled in the art that various changes in form and details may be made without departing from those principles. The invention should therefore be interpreted to encompass all such variations coming within the spirit and scope of the appended claims.

What is claimed is:

1. A sample holder for holding a scanning electron microscope sample (SEM) comprising:
   a holder body comprising a sample holding portion configured to receive and hold a SEM sample;
   a first opening located in the sample holding portion, said first opening configured to receive the sample; and
   an elastic member configured to supply a holding force to hold the sample in the first opening.

2. The sample holder of claim 1, further comprising a second opening located adjacent the first opening, wherein a sample holding member is located in the second opening.

3. The sample holder of claim 2, wherein the sample holding member comprises:
   a main body configured to contact a longitudinal end of a sample inserted into the first opening; and
   a lower lip protruding from the main body, said lower lip configured to contact a lateral side of the sample mounted in the first opening.

4. The sample holder of claim 3, wherein a width of the second opening is greater than a width of the first opening.

5. The sample holder of claim 3, wherein a height of an upper surface of the lower lip is lower than a height of an upper surface of the main body.

6. The sample holder of claim 3, wherein a protrusion is disposed on the upper surface of the main body of the sample holding member.

7. The sample holder of claim 3, wherein a forward end of the lower lip of the sample holding member is rounded.

8. The sample holder of claim 2, further comprising an elastic member insertion groove arranged in the holder body in communication with the second opening, wherein a first end of the elastic member is inserted into the elastic member insertion groove, and wherein a second end of the elastic member is arranged in contact with the sample holding member.

9. The sample holder of claim 2, wherein the sample holding member is capable of longitudinal movement within the second opening.

10. The sample holder of claim 9, wherein the sample holding member is biased in a forward position by the holding force supplied by the elastic member.

11. The sample holder of claim 2, further comprising a third opening disposed along a side of the first opening and configured to permit easy insertion and removal of the sample into and from the first opening.

12. The sample holder of claim 11, wherein a depth of the third opening is less than a depth of the first opening, and wherein a corner at an interface between the first and third openings is rounded or beveled.

13. The sample holder of claim 1, wherein a catch is formed on a lower portion of an external surface of the holder body of the sample holder.

14. The sample holder of claim 1, wherein the elastic member is a compression spring configured to resist compression to generate the holding force.

15. The sample holder of claim 1, wherein the elastic member is a tension elastic member that uses a tension-resistant force to supply the holding force.

16. A wafer sample holder for use in a scanning electron microscope (SEM) comprising:
   a holder body;

a wafer sample holding portion located in a forward portion of the holder body;

a first opening located on a side of the wafer sample holding portion wherein the first opening has a depth and length sized for receiving and holding a wafer sample, further wherein the length of the first opening extend parallel to the length of the holder body;

a wafer sample holding member; and, an elastic member for applying an elastic force to the wafer sample holding member to hold the wafer sample in the first opening.

17. The sample holder of claim 16 further including the elastic member configured to apply an elastic force to the wafer sample holding member in a direction parallel to the length of the wafer sample.

18. The sample holder of claim 16, wherein the elastic member is a compression spring configured to resist compression to generate the holding force.

19. The sample holder of claim 16, wherein the elastic member is a tension elastic member that uses a tension-resistant force to supply the holding force.

20. The sample holder of claim 16, further including a second opening located in the sample holding portion adjacent to the first opening and in communication with the first opening.

21. The sample holder of claim 20, wherein the wafer sample holding member is located in the second opening, further including a protrusion extending outward from the wafer sample holding member through the second opening for moving the holding member in loading and unloading of wafer samples.

22. A sample holder comprising:

a mostly cylindrically shaped holder body with front and rear ends;

a first opening for holding a sample located at the front end of the holder body, said opening sized in a depth and a length for receiving a sample and said length extending parallel to the holder body;

a sample holding member located adjacent to the first opening toward the rear end of the holder body;

an elastic member that exerts an elastic force on the sample holding member to hold a sample in the first opening; and wherein the first opening is shaped such that a longitudinal portion of predetermined thickness is removed from the front end of the cylindrically shaped holder body and a groove of further thickness is positioned along the longitudinal portion.

23. The sample holder of claim 22, further including a second opening is located longitudinally adjacent to the first opening, wherein the second opening is sized to receive the sample holding member and the elastic member.

24. The sample holder of claim 23, further including a protrusion on the sample holding member extending outward of the second opening for operation of the sample holder.

* * * * *